United States Patent [19]

Taylor

[11] Patent Number: 4,492,832
[45] Date of Patent: Jan. 8, 1985

[54] HAND-CONTROLLABLE SWITCHING DEVICE FOR ELECTROSURGICAL INSTRUMENTS

[75] Inventor: Glenn N. Taylor, Longmont, Colo.

[73] Assignee: Neomed, Incorporated, Boulder, Colo.

[21] Appl. No.: 452,450

[22] Filed: Dec. 23, 1982

[51] Int. Cl.³ .................. H01H 35/00; H01H 13/08; A61B 17/36

[52] U.S. Cl. .................. 200/52 R; 128/303.13; 200/157

[58] Field of Search .............. 200/52 R, 61.55, 61.57, 200/61.85, 85 R, 86 R, 157, 275; 128/303.13, 303.14, 303.17

[56] References Cited

U.S. PATENT DOCUMENTS

| Re. 29,088 | 12/1976 | Shaw | 128/303.17 |
|---|---|---|---|
| 3,532,095 | 10/1970 | Miller et al. | 128/303.13 |
| 3,648,001 | 3/1972 | Anderson et al. | 200/157 |
| 3,799,168 | 3/1974 | Peters | 128/303.14 |
| 3,870,047 | 3/1975 | Gonser | 128/303.14 |
| 3,911,241 | 10/1975 | Jarrard | 200/157 |
| 3,920,021 | 11/1975 | Hiltebrandt | 128/303.17 |
| 3,935,405 | 1/1976 | Aver | 200/85 R X |
| 3,974,833 | 8/1976 | Durden | 128/275.1 |
| 4,014,343 | 3/1977 | Esty | 128/303.14 |
| 4,032,738 | 6/1977 | Esty et al. | 200/157 |
| 4,043,342 | 8/1977 | Morrison, Jr. | 128/303.14 |
| 4,076,028 | 2/1978 | Simmons | 128/303.13 |
| 4,103,688 | 8/1978 | Edwards | 128/303.17 |
| 4,112,950 | 9/1978 | Pike | 128/303.14 |
| 4,128,099 | 12/1978 | Bauer | 128/303.17 |

FOREIGN PATENT DOCUMENTS 2460481  6/1976  Fed. Rep. of Germany .

*Primary Examiner*—J. R. Scott
*Attorney, Agent, or Firm*—John E. Reilly

[57] ABSTRACT

A hand-controllable switch for remote control of an electrosurgical instrument is comprised of an elongated hollow body composed of an electrically insulative material with an electrical conductor tube positioned therein, a blade member inserted lengthwise through a bore in connected relation to the conductor tube, and electrical leads terminating in longitudinally spaced relation to one another so that in contacting the conductor tube they are operative to establish distinct electrical power levels. The body is composed of a resilient material in which is resiliently mounted one or more annular switch members which are depressible under hand or finger pressure at any point on their circumferences to effect closure with the electrical conductor tube.

16 Claims, 6 Drawing Figures

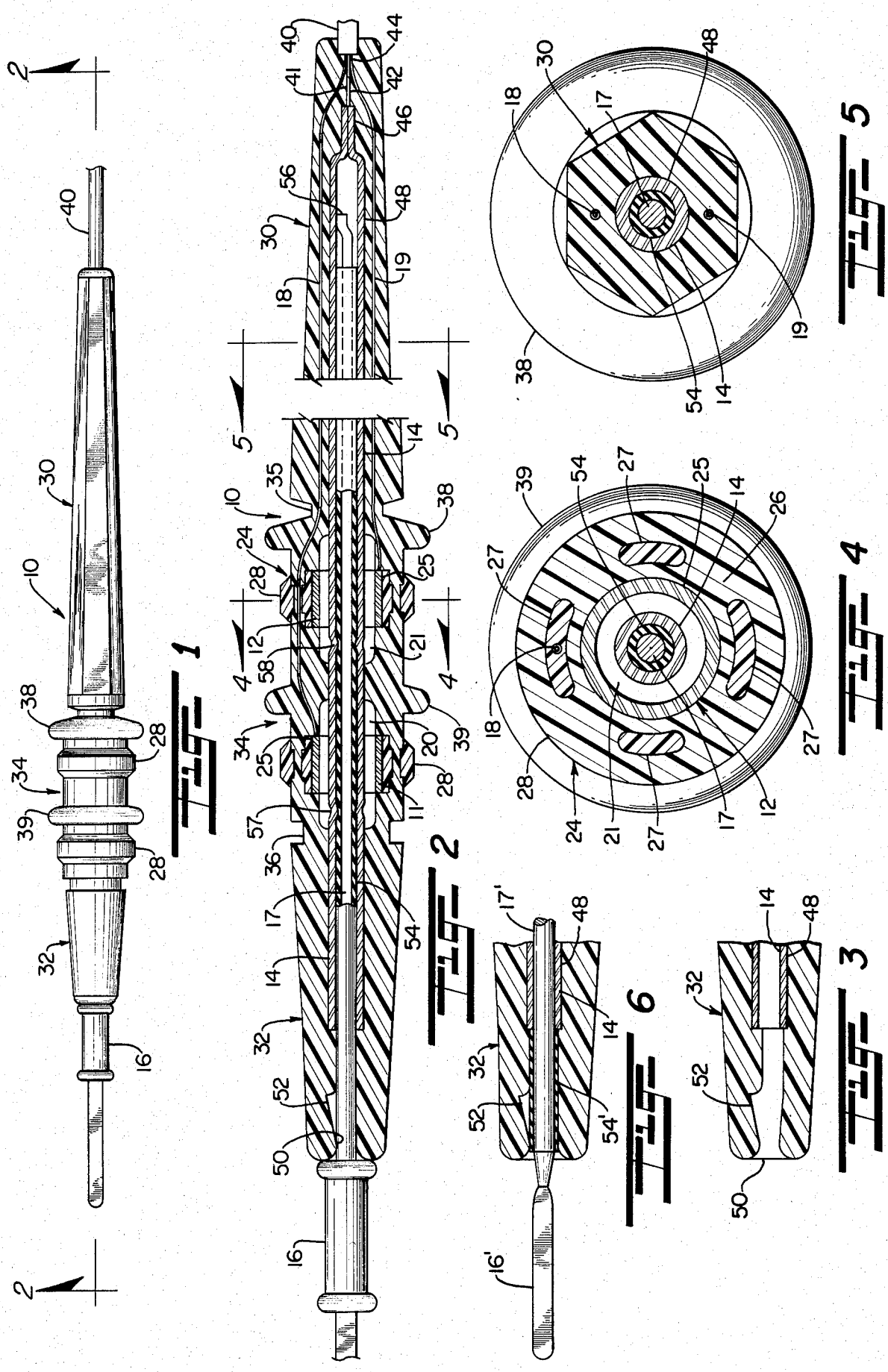

HAND-CONTROLLABLE SWITCHING DEVICE FOR ELECTROSURGICAL INSTRUMENTS

This invention relates to hand-controlled switching devices, and more particularly relates to a novel and improved switching device which is controllable to establish the desired mode of operation of an electrosurgical generator in performing surgical procedures.

BACKGROUND AND FIELD OF THE INVENTION

Hand-controlled switches are employed in numerous applications and are generally characterized by having normally open switch contacts which can be closed by the application of hand pressure to one of the contacts in the housing of the switch. The switching device of the present invention may be best exemplified by reference to its use in electrosurgery to permit selection of a particular electrosurgical function, such as, to establish the desired power level for cutting or coagulation through a blade or other tool which is directly attached to the switching device. Among the desirable features of switching devices used for this purpose are to permit ease of interchangeability of different lengths and types of blades; to effect a complete seal between the blade and switching elements; and to permit the surgeon to easily discern by hand pressure or feel the identity of each switch setting irrespective of shifting or placement of the hand on the switching device. It is equally important that the surgeon be able to change the position of the hand or fingers on the switching device, for instance, in manipulating or changing the blade angle or position while retaining complete control over the switch setting.

Representative patents directed to hand switching devices for electrosurgical instruments include U.S. Pat. Nos. 3,911,241 to J. W. Jarrard; 4,014,343 to J. M. Esty; and 4,032,738 to J. M. Esty et al; all of which are assigned to assignee of the present invention. Other representative patents are U.S. Pat. Re. Nos. 29,088 to R. F. Shaw; 3,532,095 to A. K. Miller et al; 3,799,168 to R. W. Peters; 3,870,047 to D. I. Gonser; 3,920,021 to S. Hiltebrandt; 3,974,833 to J. G. Durden, III; 4,043,342 to C. F. Morrison, Jr.; 4,076,028 to R. W. Simmons; 4,103,688 to J. Edwards; 4,112,950 to H. L. Pike; and 4,128,099 to S. Bauer. Finally, Federal Republic of Germany Pat. No. 24 60 481 to E. Roos discloses a ring-like contact member which can be squeezed inwardly into engagement with two other spaced ring-like contacts to effect closure, but does not suggest a way of pressing one or more contact bands inwardly into engagement with a central contact which serves also to support the knife or tool of the switching device.

It is therefore proposed in accordance with the present invention to provide a one-piece pliable body or casing unit which can be molded into unitary relationship to the outer switching elements and in outer spaced but surrounding relation to a single inner switching element or electrical conductor in such a way as to permit positive switching and a clear definition between the different modes of operation; and further to permit switching over a 360° arc on the body at each switch position so as not to require removal or changing the position of the blade when a directional change in the blade is called for in the surgical operation. Furthermore, it is highly desirable to establish complete interchangeability between different types and lengths of blades which are releasably supported, at least in part, by the central contact or conductor element and to effect a water-tight construction so as to completely seal the switching elements when the blade is inserted in position therein.

SUMMARY OF THE INVENTION

It is therefore an object of the present invention to provide for a novel and improved hand-controllable switching device, particularly of the type which is capable of establishing different selected modes of operation of an electrosurgical generator in performing surgery.

Another object of the present invention is to provide for a novel and improved switching device comprised of a one-piece pliable body construction which is unitized with hand-switchable means which will enable close hand control and reliable switching action when held at virtually any position or angle with respect to the operation to be performed.

It is a further object of the present invention to provide for an electrosurgical switching device which is hermetically sealed and permits interchangeable insertion of different lengths and types of blades but which will securely retain the blade in position against shifting and movement once inserted; and further wherein the body is capable of permitting length adjustment of each blade within the switching device depending on the specific operation to be performed.

It is an additional object of the present invention to provide for a remote control, electrosurgical hand-switching device which is versatile and conformable for use with different blades and tools directly attached thereto with ease of sensing of each switch position and where switching can be accomplished over a 360° arc on the surface of the switching device.

In accordance with the present invention a hand-controllable switch is comprised of an elongated hollow body is composed of an electrically insulative material with an electrical conductor inserted through one end and a tool inserted lengthwise through the opposite end for electrical connection with the electrical conductor. At least one electrical lead extends through the body in outer concentric relation to the electrical conductor and an annular contact member is disposed in the body in normally outer, spaced concentric relation to the electrical conductor. The body includes means for resiliently mounting the annular switch member so that it is depressible under hand pressure at any point on its circumference to effect closure with the electrical conductor.

In its preferred form, the invention is comprised of a hand-controllable switch for remote control of an electrosurgical instrument in which an elongated, pliable hollow body of electrical insulating material has an electrical conductor tube centrally disposed therein, a blade member inserted lengthwise through a bore at one end of the body in connected relation to the conductor tube, and electrical leads terminating in longitudinally spaced relation to one another so that in contacting the conductor tube are operative to establish distinct electrical power levels. Longitudinally spaced contact rings are embedded in the body, each ring connected to one of the leads and disposed in normally outer spaced concentric relation to the conductor tube so that when the ring is displaced under radially inwardly directed pressure it will engage the conductor tube for application of power at the predetermined level established by its associated lead to the blade. Associated features of the switch device reside in the ability to accommodate blades of different types with shank portions of differing lengths which are releasably insertable into engagement with the conductor tube and may be adjusted to project the desired effective length away from the tube. In order to enhance the gripping action of the body with respect to the knife shank, preferably the bore at the blade-receiving end of the body is normally offset with respect to the conductor tube but is displaced by the shank portion of the knife into axial alignment with the tube when the shank portion is inserted therethrough.

Other objects, advantages and features of the present invention will become more readily appreciated and understood when taken together with the following detailed description in conjunction with the accompanying drawings, in which:

BRIEF DESCRIPTION OF THE DRAWINGS

FIG. 1 is a side view in elevation of a preferred form of switching device for electrosurgical instruments in accordance with the present invention;

FIG. 2 is a longitudinal section view taken about lines 2—2 of FIG. 1;

FIG. 3 is a fragmentary section view of the front blade-receiving end of the preferred form of the device shown in FIGS. 1 and 2 with the blade removed;

FIG. 4 is a cross-sectional view through one of the switch settings taken about lines 4—4 of FIG. 2;

FIG. 5 is a cross-sectional view taken about lines 5—5 of FIG. 2; and

FIG. 6 is a cross-sectional view similar to FIG. 3 illustrating the releasable insertion of a modified form of knife therein.

DETAILED DESCRIPTION OF THE PREFERRED EMBODIMENT

Referring in detail to the drawings, there is illustrated in FIGS. 1 to 5 a preferred form of hand-controllable switching device for electrosurgical instruments which is broadly comprised of an elongated hollow body 10 containing a pair of longitudinally spaced switch contact elements 11 and 12 arranged in outer spaced concentric relation to an electrical conductor 14 extending longitudinally through the greater length of the body from a point adjacent to one end thereof. The electrical conductor 14 is preferably in the form of a rigid tube sized to permit releasable insertion of the shank end of a blade 16 which extends through the opposite end of the switching device to that of the electrical conductor. Electrical leads 18 and 19 extend through the body from the one end for connection to the switch contact elements 11 and 12, respectively. The switch contact elements 11 and 12 each is correspondingly formed of a substantially rigid metal ring or band positioned to extend circumferentially along inner walls of cavities or recessed areas 20, 21 in the body so that when either of the switch contact elements 11 and 12 is pressed in a radially inward direction, it will make contact with the electrical conductor to effect closure of the switch.

Considering in more detail the construction and arrangement of the switching assembly, preferably each of the switch contact elements 11 and 12 is affixed to an inner wall surface of a collar 24, each collar 24 having an inner flat seating portion 25, a radially extending web 26 provided with circumferentially spaced apertures 27 and an outer circular rim 28. Each collar 24 is preferably composed of a somewhat inflexible or rigid material with an inner circular seating portion 25 of a width less than the length of the cavity 20 or 21 within which it is positioned, and the rim 28 is dimensioned to project beyond the external wall surface of the body 10.

The apertures 27, as best seen from FIG. 4, have the principal function of permitting the material of the body 10 to flow through the collars 24 in the process of molding or curing of the body in a manner to be described into unitary relation to the collars; also, one of the apertures 27, as illustrated in FIG. 2, permits extension of one of the leads 18 through the collar 24 which contains the ring 12 into connected relation to the contact ring 11. The other lead 19 is connected to the collar 12, each lead establishing different power levels for the knife.

Now turning to a more detailed consideration of the construction and arrangement of the body 10, preferably the body is defined by a pliable elongated casing having a slender tapered electrical conductor-receiving end 30 and a thickwalled forwardly tapered, blade-receiving end 32 which are interconnected by an intermediate switch housing portion 34. The intermediate switch housing portion 34 is divided from opposite ends 30 and 32 by circumferential grooves 35 and 36, respectively. The groove 35 merges into an enlarged circumferential rib 38 located adjacent to the rim or button 28 surrounding the contact ring 12, and another rib 39 is located on the opposite side of the rim 28 surrounding contact ring 12 and just rearwardly of the forwardmost rib 28 for contact ring 11. The spaced ribs 38 and 39 facilitate grasping of the hand switching device and ease of identification by the surgeon of each of the circular control buttons 28 for the contact rings 11 and 12.

The leads 18 and 19 extend in diametrically opposed relation to one another through the thickness of the body from a cable 40 which is positioned at the extremity of the electrical conductor-receiving end 30, and a pair of additional leads 41 and 42 extend from the cable through a limited aperture 44 at the rearward extremity of the housing, the leads 41 and 42 being fixed by crimping the end 46 of the conductor tube 14. The body 10 is provided with a main bore 48 for insertion of the conductor tube 14, the main bore being interrupted only by the intermediate cavities 20 and 21 which as referred to earlier are slightly enlarged with respect to the diameter of the main bore and with the contact rings 11 and 12 mounted in flush relation to the walls of the cavities 20, 21.

Preferably, the blade-receiving end 32 is relatively thick-walled with respect to the conductor-receiving end 30 and is provided, as best seen from FIG. 3, with a counterbore 50 which is normally offset with respect to the longitudinal axis of the main bore 48 and has an inner stepped portion or shoulder 52. Thus, when the shank portion 17 of the blade 16 is inserted into the counterbore 50 it will cause its expansion or displacement from the relationship shown in FIG. 3 to that shown in FIG. 2 while being firmly gripped and frictionally engaged by the inner wall surface of the counterbore 50. As further illustrated in FIG. 2, the shank portion 17 has an outer sleeve 54 composed of a non-conductive material which will serve to snugly position the shank portion of the blade within the conductor tube 14. In the case of a longer blade, as shown in FIG. 2, the innermost extremity 56 is laterally offset to project beyond the sleeve 54 and bear against the inner surface of the conductor tube 14. The conductor tube may be provided with indentations 57, 58 at longitudinally spaced intervals so that in positioning the shank end of the blade within the body 10 the surgeon can adjust the effective length of the blade which projects beyond the end 32 by sensing the engagement of the offset extremity 56 with the indentations 57 and 58. Additional indentations may be formed at spaced intervals as desired.

By virtue of the construction of the blade-receiving end 32 of the body 10, as illustrated in FIG. 6, a relatively short blade 16' may be attached in place of the blade 16 illustrated in FIG. 2. Thus, the blade 16' has a shank 17' covered with an insulating sleeve 54', the shank end 17' extended but a limited distance into the interior of the conductor tube 14.

In the fabrication of the switch assembly, it will be evident that the collars 24 can be separately assembled with attached contact rings 11 and 12. The assembled collars 24 are then positioned in a mold, not shown, with the conductor tube 14 and leads 18 and 19 positioned such that the lead 18 extends through the rearwardmost collar 24 and is electrically connected to the contact ring 11 while the lead 19 is connected to the contact ring 12. The body is then molded as a one-piece structure which will flow through and around the collars 24, and a temporary arbor is positioned centrally of the mold to define the desired interior configuration of the body wall and cavities 20, 21 with the inner contact rings 11 and 12 disposed in outer surrounding relation to the arbor, not shown. Once the body has solidified and cured, the temporary arbor is removed and the conductor tube 14 inserted into position as shown with the cable end portion 40 affixed, such as, with a suitable bonding agent to the end of the body in surrounding relation to the leads 41, 42 which project from the crimped end 46 of the conductor tube. Thus, in a one-step operation, the body can be integrated completely into unitary relation to the collars and connected leads 18 and 19. It will be evident that as a suitable alternative in the molding operation the conductor tube 14 can be employed in place of the temporary arbor in the molding operation but would require disposition of spacers on the tube for the formation of the cavities 20, 21. The spacers, not shown, would be suitably composed of a material which would disintegrate once the body material had at least partially solidified so as to permit removal of the spacer material from the blade-receiving end. As shown in FIG. 5, the cable-receiving end 30 may be given a generally polygonal configuration while the ribs 38 and 39 are given a circular configuration.

In accordance with conventional practice, the leads 18, 19 are connected along with the cable to an external power supply which will apply different power levels depending upon which of the switch contact elements 11 or 12 is depressed into engagement with the conductor tube 14. The positioning of the ribs 38, 39 is such that the surgeon can readily discern which of the switch elements is to be depressed for the desired power setting. In this relation, the body is preferably composed of an elastomeric material which possesses the necessary resiliency that it will normally retain the switch contact rings 11 and 12 in an open position but will permit depression of the elements into contact with the ring under positive hand or finger pressure. A particular advantage to be noted is that the switch is operational over a 360° arc or, in other words, the entire circumference of the body so as to obviate removal of the blade when a change in blade position is called for. Typical materials which can be employed in the construction of the body are natural or synthetic rubber or rubber-like materials, such as, the Neoprene elastomers, vinyl or silicon materials. A preferred composition is a thermoplastic material sold by Shell Chemical Company under the trademark Kraton G2705. In this respect, when the blade is inserted through the blade-receiving end 32, the counterbore 50 will operate as a complete seal to prevent the intrusion or leakage of fluids into the interior of the blade which could otherwise cause malfunctioning of the contact elements.

It is therefore to be understood from the foregoing that various modifications and changes may be made in the construction and arrangement of parts as well as their method of fabrication without departing from the spirit and scope of the present invention as defined by the appended claims.

I claim:

1. A hand-controllable electrical switching device comprising an elongated hollow body composed of electrically insulative material, an elongated electrical conductor positioned longitudinally within the hollow interior of said body and being hollow at one end, a tool inserted lengthwise through one end of said body into said hollow end of said electrical conductor for electrical connection therewith, and at least one electrical lead extending into said body in spaced relation to said electrical conductor; and an annular contact member disposed in said body in normally outer, spaced concentric relation to said electrical conductor and connected to said electrical lead, and means resiliently mounting said annular contact member normally away from contact with said electrical conductor and said annular contact member being depressible under hand pressure at any point on the circumference of said body surrounding said annular contact member to cause said annular contact member to move into contact with said electrical conductor.

2. A switch device according to claim 1, said annular contact member being in the form of a metallic ring embedded in said body.

3. A switch device according to claim 1, there being a pair of annular contact members in the form of longitudinally spaced metallic rings, each embedded in an inner wall of said body and each being independently depressible to effect closure with said electrical conductor, there being a pair of said electrical leads with one of said leads connected to each of said metallic rings.

4. A switch device according to claim 1, said body having an enlarged circumferential divider portion on its external wall surface between said metallic rings for ease of identification of the relative location of each of said metallic rings.

5. A switch device according to claim 4, said divider portion defined by a circumferential rib on the external wall of said body.

6. A switch device according to claim 1, said body provided with a pair of offset longitudinal bores extending through opposite ends of said body into communication with one another, one of said longitudinal bores receiving said electrical conductor and the other of said longitudinal bores receiving said tool.

7. A switch device according to claim 6, said body composed of a pliable material in surrounding relation to said other of said longitudinal bores such that said other of said longitudinal bores is displaced into alignment with said one longitudinal bore when said tool is inserted therein.

8. A hand-controllable switching device adapted for use in controlling the application of electrical current between an electrosurgical generator and a surgical electrode, comprising:

an elongated hollow body composed of electrically insulative material, an elongated hollow tubular electrical conductor positioned in the hollow interior of said body and extending the greater length of said body, a knife provided with a shank portion inserted lengthwise through one end of said body into electrical connection within one end of said tubular electrical conductor, and at least one electrical lead extending through said body in spaced relation to said electrical conductor and; an annular contact band disposed in said body in normally outer, spaced concentric relation to said electrical conductor and connected to said electrical lead, said body being composed of resilient material, and means for mounting said annular contact band in said body whereby said annular contact band is depressible from outside said body under hand pressure at any point on its circumference into electrical contact with said electrical conductor tube.

9. A switching device according to claim 8, said annular contact band embedded in an inner wall of a cavity formed in said body.

10. A switching device according to claim 9, including a pair of said annular contact bands in longitudinally spaced relation to one another, each embedded in an inner wall of said body, each said electrical lead connected to one of said bands, and an enlarged circumferential rib portion on said body between said bands.

11. A hand-controllable switch for remote control of an electrosurgical instrument comprising:

an elongated pliable hollow body of electrical insulating material having a longitudinal, tubular electrical conductor centrally disposed therein, a blade inserted lengthwise through a bore at one end of said body into inner concentric connected relation to said electrical conductor, and a pair of electrical leads terminating in longitudinally spaced relation to one another, each of which is operative to establish distinct electrical power levels; and longitudinally spaced contact rings embedded in said body, each said ring connected to one of said leads and disposed in normally outer spaced concentric relation to said electrical conductor, each said ring displaceable under radially inwardly directed pressure to contact said electrical conductor for application of power at a distinct predetermined level to said blade.

12. A hand-controllable switch according to claim 11, said body having a circumferential rib projecting radially outwardly from its external surface between said contact rings.

13. A hand-controllable switch according to claim 11, including a series of circumferential ribs projecting radially outwardly from said body at longitudinally spaced intervals to define depressions therebetween in the external wall of said body and in outer concentric relation to said contact rings.

14. A hand-controllable switch according to claim 11, said body provided with a pair of longitudinal bores extending through opposite ends of said body into communication with one another, one of said longitudinal bores receiving said electrical conductor and the other of said longitudinal bores receiving said knife, said other of said longitudinal bores being normally offset with respect to said one of said longitudinal bores and being displaced by said knife into alignment with said one longitudinal bore.

15. A hand-controllable switch according to claim 11, a cable secured to an end of said body opposite to said one end, said cable including said one pair of leads connected to said contact rings and a second pair of leads connected to an end of said electrical conductor.

16. A hand-controllable switch according to claim 11, said electrical conductor having longitudinally spaced indentations therein, said blade having a shank inserted into said tubular conductor including an offset portion therein engageable with said indentations.

* * * * *